United States Patent [19]

Montealegre

[11] 4,279,373
[45] Jul. 21, 1981

[54] AIR FRESHENER CARTON

[75] Inventor: James Montealegre, West St. Paul, Minn.

[73] Assignee: Champion International Corporation, Stamford, Conn.

[21] Appl. No.: 108,005

[22] Filed: Dec. 28, 1979

[51] Int. Cl.³ .................... B65D 13/06; B65D 5/38; A61L 9/04

[52] U.S. Cl. .................................... 229/11; 239/57; 239/59

[58] Field of Search .................. 229/9, 10, 11, 19, 20; 239/59, 60, 57

[56] References Cited

U.S. PATENT DOCUMENTS

| | | | |
|---|---|---|---|
| 1,994,159 | 3/1935 | Wurzburg | 229/9 X |
| 2,247,600 | 7/1941 | Brennsan et al. | 239/59 X |
| 2,354,239 | 7/1944 | Williamson | 229/19 X |
| 2,683,953 | 7/1954 | Hopkins | 229/11 UX |
| 3,302,844 | 2/1967 | Henry | 229/10 |
| 3,761,009 | 9/1973 | Rosenburg, Jr. | 229/11 X |
| 4,220,281 | 9/1980 | Martens et al. | 239/59 X |

Primary Examiner—Davis T. Moorhead
Attorney, Agent, or Firm—Evelyn M. Sommer

[57] ABSTRACT

A carton for releasing an active material, such as an air freshener, to the atmosphere includes an outer imperforate sleeve slidably receiving in nesting relation an inner sleeve housing an air freshener cake. The inner sleeve has a plurality of openings for exposing the cake of air freshener material to the atmosphere as the openings are selectively exposed by sliding the inner sleeve relative to the outer sleeve. The inner sleeve is slidable between a first position defined by abutment with the scaled closure of the outer sleeve and a second position intermediate the end containing the sealed closure of the outer sleeve and the opposite end thereof so as to selectively expose certain ones of the openings in the inner sleeve. The inner sleeve contains a sealed closure having a panel extending outwardly beyond the side panels thereof for contact with a pair of locking tabs on the bottom edge of the outer sleeve to preclude disassembly of the first and second sleeves.

4 Claims, 11 Drawing Figures

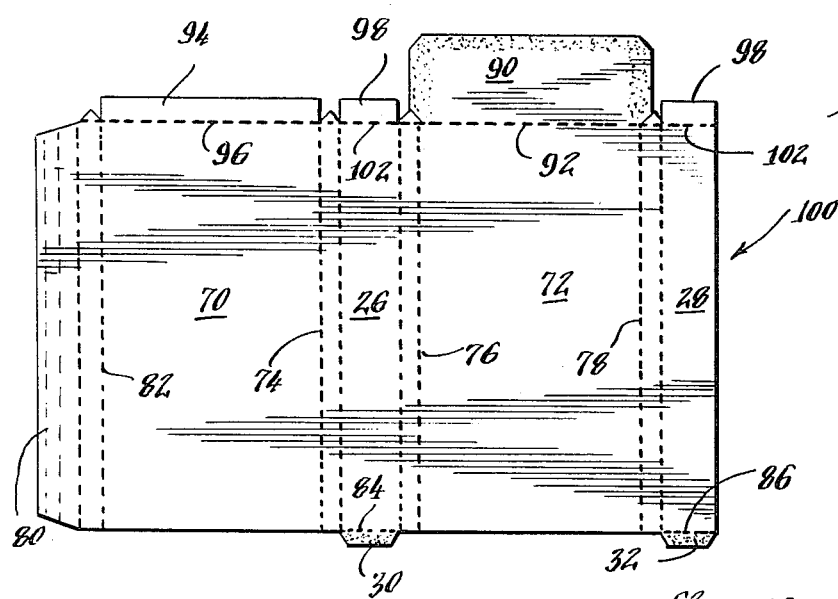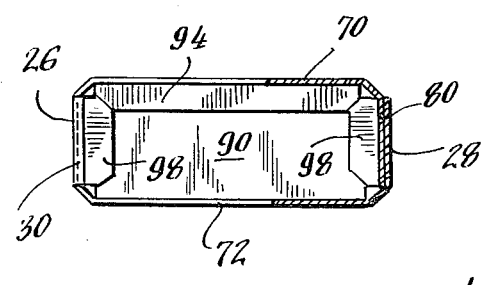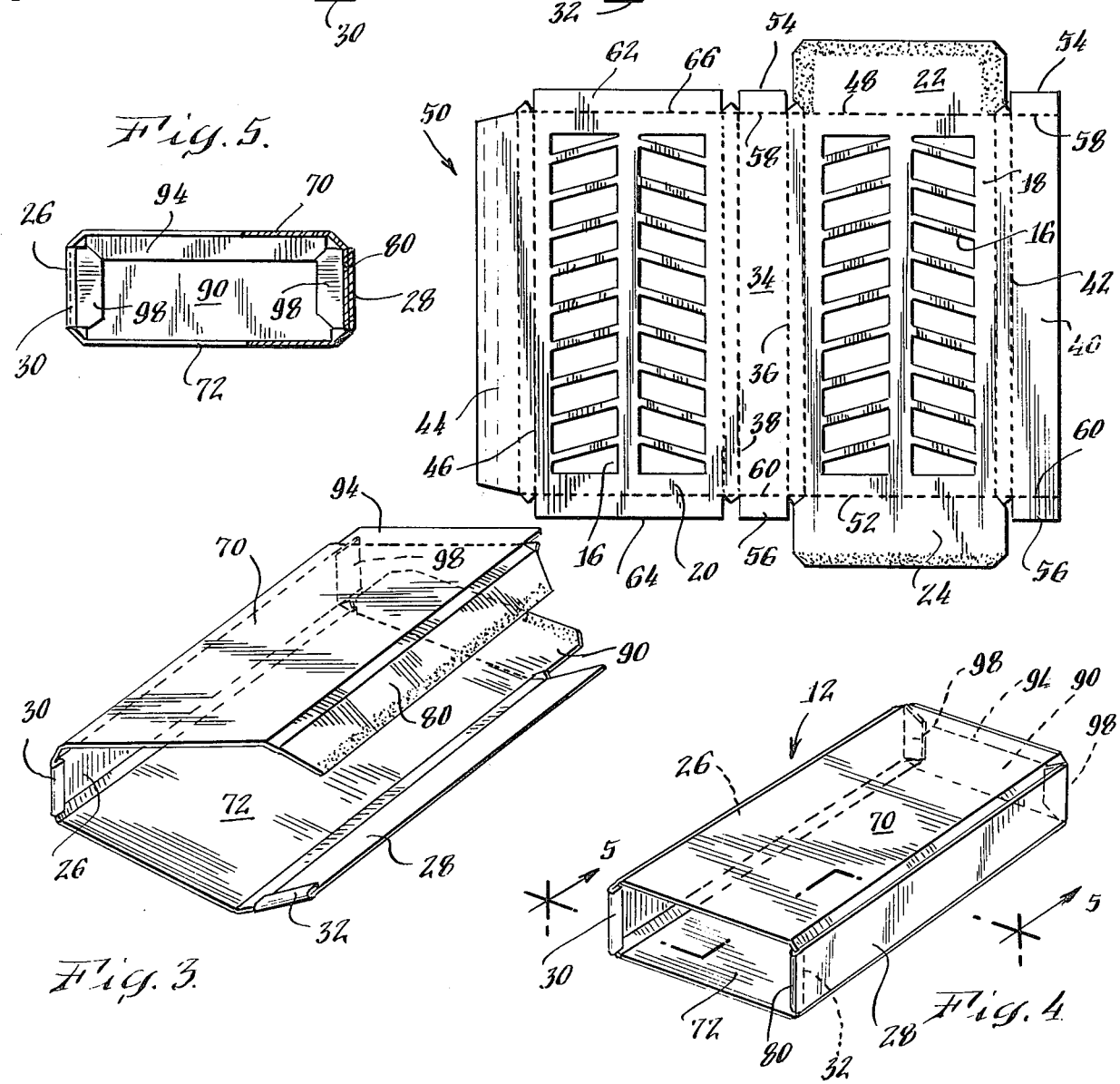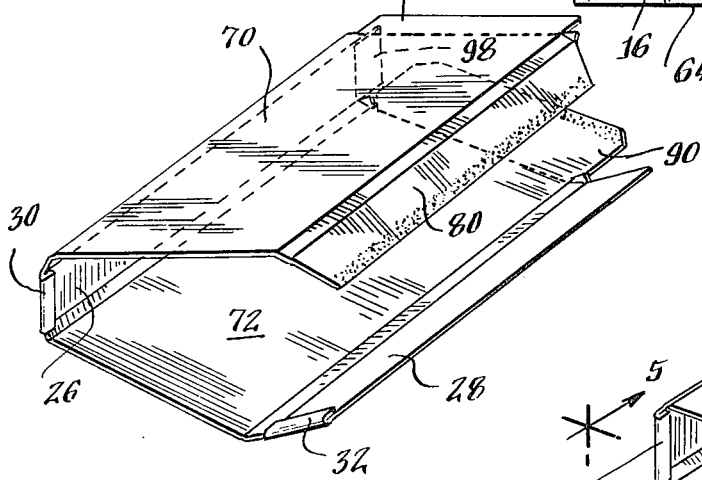

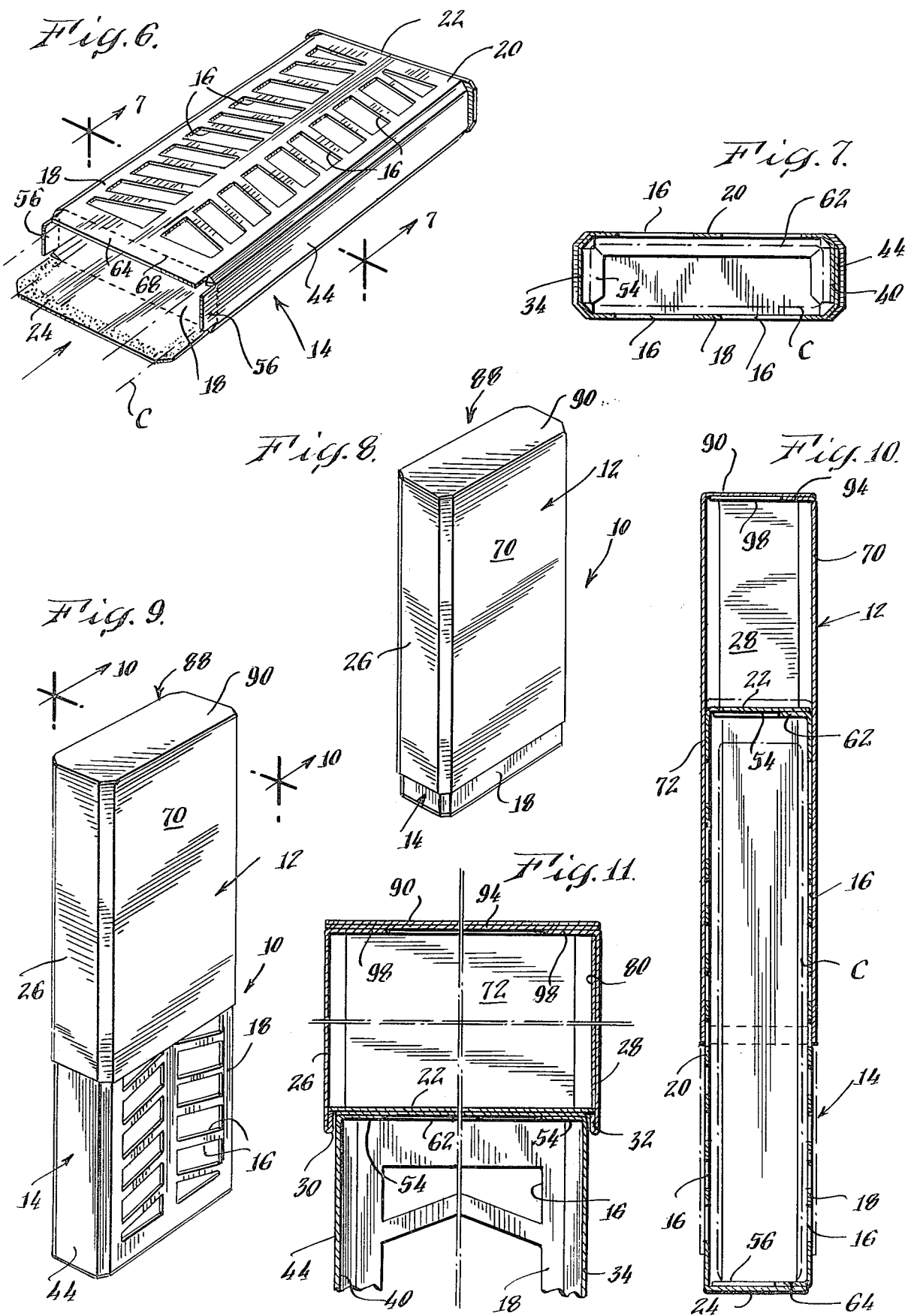

AIR FRESHENER CARTON

BACKGROUND OF THE INVENTION

1. Field Of Invention

The present invention relates to cartons, and more particularly to a carton for holding an active material and controllably releasing it to the air.

2. Description Of The Prior Art

There are a variety of active materials for use in household and commercial applications which it is desirable to contact with and release into the ambient air. Among these are insecticides and air fresheners which can be packaged in solid form in containers having air passages which permit release. Frequently, products of this type are packaged in containers having a plurality of openings which are closed at the time of purchase but which are opened at the time of use to allow room air to circulate over the surface of the solid active material.

In one type of carton, the openings are covered with a panel of release paper. When the consumer is ready to use the product, such as an air freshener, the release paper is peeled from the face of the container to allow room air to begin circulating through the openings. In another type of carton, the consumer activates the air freshener material by squeezing to release an encapsulated active ingredient. In yet another type of carton, holes in an outer carton wall are opened or closed by a slidable inner sheet which acts as a valve.

Molded plastic containers, usually consisting of a molded shell and a separate molded cover, have been employed to hold air freshener material. However, while molded plastic containers have an aesthetically pleasing appearance, the cost of making them is higher than might be desired. The shell and cover must be molded in separate operations and stored in unassembled form until the air freshener insert is loaded. The cover then must be glued or otherwise secured to the shell to provide a closed container. The extra time required for the separate manufacturing and assembly operations results in added manufacturing costs for the package and ultimately for the product sold therein. The fact that the molded shells and covers must be shipped and stored in their molded form will also cause increased transportation and storage costs.

In a prior patent application, U.S. Ser. No. 025,012 filed Mar. 29, 1979 entitled "CARTON WITH ADJUSTABLE AIR PASSAGES", assigned to the same assignee as the present invention, an improved package for controllably releasing active materials to the air is disclosed which has inner and outer slidable members constructed of a sheet material wherein the inner and outer members can be slidably moved between open and closed positions. The carton has a plurality of adjustable air passages and comprises: (a) a first tapered sleeve forming an outer carton unit, said first sleeve being closed at at least one end and having a plurality of spaced openings therein; and (b) a second tapered sleeve forming an inner carton unit, said second sleeve being nested within said first sleeve and being slidable between a first position and a second position, said second sleeve being closed at at least the end opposite said end closed in said first sleeve and having a plurality of spaced openings therein arranged complementarily to said spaced openings in said outer carton unit to align with the openings therein when said inner carton unit is in said first position, and to align with the spaces between said openings in said outer carton unit when said inner carton unit is in said second position.

When the openings are aligned, they permit air to circulate through the openings into the interior of the inner carton unit to permit the release or diffusion of material housed within the inner unit to the air. The tapered sleeves normally bind when moved relative to each other to preclude disassembly and when the openings are out of alignment, the diffuser is inoperative, as the openings in the inner unit are closed.

SUMMARY OF THE INVENTION

The present invention relates to an improved carton of the type having an inner and outer carton unit for use in dispensing an active material to the atmosphere.

The sides of the inner and outer unit do not taper, but rather locking tabs are provided on the lower edge of the outer unit for engagement with an oversized seal tab on the upper end of the inner unit which precludes the units from becoming disassembled or separated.

Further, the outer unit does not contain openings, but is a solid sleeve which receives the inner unit in longitudinal, sliding engagement. The inner unit does contain a plurality of openings on two facing, major panels through which air can circulate about a cake of active material, such as air freshener material. In order to diffuse the active material to the atmosphere, it is only necessary to slide the inner carton unit relative to the outer carton unit or sleeve to expose the openings to the atmosphere. When not in use, the inner carton unit is housed completely within the sleeve.

The inner and outer carton unit arrangement described results in a simplier unit to manufacture, assemble and use.

BRIEF DESCRIPTION OF THE DRAWINGS

The invention will be better understood and its advantages will be more apparent from the following detailed description and claims, and from the accompanying drawings, wherein:

FIG. 1 is a plan view of a blank for forming the outer unit or sleeve of the carton of the present invention;

FIG. 2 is a plan view of a blank for forming the inner unit of the carton of the present invention;

FIGS. 3 and 4 are perspective views illustrating the blank of FIG. 1 being folded to form the outer unit or sleeve of the carton of the present invention;

FIG. 5 is a cross-sectional view taken substantially along the planes indicated by line 5—5 of FIG. 4;

FIG. 6 is a perspective view illustrating the blank of FIG. 2 folded to form the inner unit of the carton of the present invention;

FIG. 7 is a cross-sectional view taken substantially along the plane indicated by line 7—7 of FIG. 6;

FIG. 8 is a perspective view of the assembled carton of the present invention in closed condition;

FIG. 9 is a view similar to FIG. 8, but with the assembled carton open to disseminate an active material to the atmosphere;

FIG. 10 is a cross-sectional view taken substantially along the plane indicated by line 10—10 of FIG. 9; and FIG. 11 is a partial, longitudinal cross-sectional view through the assembled carton of the present invention, with the carton in its fully opened condition.

DETAILED DESCRIPTION OF THE PREFERRED EMBODIMENT

Referring now to the drawings in detail, wherein like numerals indicate like elements throughout the several views, the present invention provides a two component carton 10 consisting of an outer, imperforate sleeve 12 and a relatively slidable, inner carton unit 14 housed within the outer sleeve 12. Inner carton unit 14 has a plurality of openings 16 on facing major panels 18 and 20 through which air can circulate and contact a cake C of an active material, such as an insecticide or a room air freshener, and diffuse the material to the air when the inner carton unit 14 has one or more openings 16 exposed to the atmosphere.

The inner carton unit 14 is sealed by flaps 22 and 24 at each longitudinal end to hold the cake C within the interior of inner unit 14. The top flap 22 extends slightly beyond the edges of the parallel, major panels 18 and 20 so as to frictionally engage the side walls 26 and 28 of the outer, imperforate sleeve 12. Accordingly, when the inner unit 14 is slid relative to the outer sleeve 12 (as shown in FIGS. 8 to 11), it will be retained in adjusted position by the frictional engagement of the extended side edges of seal flap 22 with the sides 26 and 28 of the outer sleeve. The outer sleeve also includes a pair of locking tabs 30 and 32 at the bottom edge of side walls 26 and 28, respectively, which are folded 180 degrees into the interior of the outer, imperforate sleeve 12 and adhesively secured to the interior of the side walls 26 and 28, respectively. The locking tabs 30 and 32 are adapted to contact the extended side edges of seal panel 22 of inner carton unit 14 to preclude the inner and outer units 12 and 14 from being disassembled, as shown in FIG. 11.

As shown in FIG. 2 the inner carton unit 14 is formed from a unitary, planar, paperboard blank generally designated by the numeral 50. Blank 50 includes the major rectangular panels 18 and 20 containing opening 16 connected by a central rectangular panel 34. Panel 34 is connected by a fold line 36 to the left edge of panel 18, while it is connected by a fold line 38 to the right edge of rectangular panel 20.

Similarly, rectangular panel 40 is connected by a hinge line 42 to the right hand edge of panel 18, while a rectangular panel 44 is connected by a hinge line 46 to the left hand edge of rectangular panel 20. The upper and lower sealing flaps 22 and 24, respectively, are foldably connected by a hinge line 48 and 52, respectively, to the upper and lower edges of major rectangular panel 18. Minor rectangular flaps 54 and 56 are connected by hinge lines 58 and 60, respectively, to the upper and lower edges of rectangular side panels 40 and 34, respectively. Generally rectangular flaps 62 and 64 are connected by hinge lines 66 and 68 to the upper and lower edges, respectively, of the other major rectangular panel 20.

The blank 50 is folded into a generally rectangular parallelepiped configuration as indicated in FIG. 6. The major panels 18 and 20 are folded about hinge lines 36 and 38, respectively, so that they face each other in parallel relationship. Panels 44 and 40 are then folded 90 degrees about their respective hinge lines 46 and 42 and adhesively connected to lie opposite and parallel to side panel 34. The cake C can then be inserted within the enclosure bounded by panels 18 and 20 as shown in FIG. 6. The ends of the enclosure are sealed by folding flaps 62 and 64 about its respective hinge lines 66 and 68, 90 degrees, overlapping side tabs 54 and 56, respectively, with panels 62 and 64, respectively, by folding the tabs 90 degrees about hinge lines 58 and 60, respectively, and then folding upper rectangular seal flap 22 downwardly about hinge line 48 and sealing it to flap 62 while closing the opposite end by folding rectangular panel 24 ninety degrees about hinge 52 and sealing it to the rectangular flap 64.

The outer imperforate sleeve 12 is also formed from a unitary, planar, paperboard blank 100, illustrated in FIG. 1.

Blank 100 includes a pair of major rectangular panels 70 and 72 joined by rectangular side wall panel 26. The panel 26 is connected to one edge of the panel 70 by a hinged line 74 while it is connected to an edge of panel 72 by a hinge line 76. Side wall panel 28 is connected to the opposite edge of the panel 72 by a hinge line 78. A third side wall panel 80 is connected to the opposite edge of the major rectangular panel 70 by a hinge line 82.

The locking tabs 30 and 32 are connected to the bottom of side wall panels 26 and 28, respectively, by hinge lines 84 and 86, respectively. A seal closure 88 is formed on the opposite end of imperforate sleeve 12 by a generally rectangular panel 90 connected to the upper edge of major rectangular panel 72 by a hinge line 92, a rectangular panel 94 connected by a hinge line 96 to the upper edge of the other major rectangular panel 70 and minor rectangular tabs 98 connected by hinge lines 102 to the upper edge of side wall panels 26 and 28, respectively.

As indicated in FIGS. 3 and 4, sleeve 12 is formed by folding panels 70 and 72 ninety degrees about hinge lines 74 and 76, respectively, so that they are spaced from each other in parallel relationship. The side panel 28 is then folded ninety degrees about hinge line 78 so as to lie parallel to side panel 26, while side panel 80 is folded ninety degrees about hinge line 82 and overlapped with panel 28 and adhesively connected thereto.

The inner sleeve 14 is then inserted in the outer sleeve 12 and the locking tabs 30 and 32 are then rotated 180 degrees about hinge lines 84 and 86, respectively, and adhered to the interior surfaces of side wall panels 26 and 28, respectively. The sealing closure 88 is then formed by folding tabs 98 inwardly ninety degrees and overlapping the same with rectangular panel 94 folded ninety degrees about hinge line 96. The other rectangular panel 90 is then folded on hinge line 92 and adhered to the upper surface of rectangular panel 94 to form the sealed closure 88 retaining the inner unit 14 within the outer sleeve 12 at its upper end.

Upper rectangular panel 22 on the inner unit 14 is slightly larger in width than the major rectangular panel 18, as shown in FIG. 11. Accordingly, when disposed within imperforate outer sleeve 12, the edges of panel 22 will frictionally ride along the interior surfaces of side wall panels 26 and 80, 28 of the outer sleeve 12 to retain the inner unit 14 in adjusted, longitudinal relation to the outer sleeve 12 as the openings 16 are selectively exposed to the atmosphere. Further, the edges of the rectangular panel 22 will contact the upturned locking tabs 30 and 32 on the outer sleeve 12 in the fully extended relative positions of inner and outer units 12 and 14 to preclude disassembly of the inner and outer carton units.

What is claimed as new is:

1. A carton for dispensing an active material to the atmosphere comprising:

a first, imperforate sleeve forming an outer carton unit, said first sleeve being a sealed closure on one end thereof, and a second sleeve forming an inner carton unit having a plurality of openings on opposed major panels thereof, said second sleeve being generally of the same cross-sectional shape as said first imperforate sleeve and being nested within said first sleeve and slidable therein between a first position defined by abutment with said sealed closure of said first sleeve and a second position intermediate the end containing said sealed closure of said first sleeve and the opposite end thereof so that certain ones of said openings in the major panels of said second sleeve unit can be selectively exposed to the atmosphere, a sealed closure on said second inner carton sleeve containing a panel extending laterally and linearly outwardly beyond side edges connecting said major panels of said second sleeve, and a locking tab on the bottom edge of the outer first sleeve adapted to contact the opposite edges of the panel extending outwardly laterally and linearly beyond the side edges connecting said major panels of said second unit to preclude disassembly of said first and second sleeves.

2. A carton in accordance with claim 1 wherein said first imperforate sleeve and second imperforate sleeve are generally rectangular in cross-section.

3. A carton in accordance with claim 2 wherein said first, imperforate sleeve includes a pair of parallel, major panels connected by a pair of parallel, minor panels, each of said locking tabs being an extension of one of said minor panels folded 180 degrees back upon itself and adhered to said minor panel to present an edge designed to contact one of said opposed edges of said sealed panel of said inner sleeve.

4. A unitary, paperboard blank for forming each of the first and second sleeves of claim 1.

* * * * *